(12) United States Patent
Sugino et al.

(10) Patent No.: US 6,265,159 B1
(45) Date of Patent: *Jul. 24, 2001

(54) METHOD FOR PRODUCING DNA NESTED DELETIONS BY AN IN VITRO REACTION USING TRANSPOSASE

(75) Inventors: Yoshinobu Sugino; Masayuki Morita; Yushi Matuo, all of Osaka; Kohji Uchida, Shiga-ken, all of (JP)

(73) Assignee: Oriental Yeast Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/998,712

(22) Filed: Dec. 29, 1997

(30) Foreign Application Priority Data

Feb. 14, 1997 (JP) .................................................. 9-030507

(51) Int. Cl.[7] .............................. C12Q 1/68; C12N 1/63; C07H 21/04
(52) U.S. Cl. ........................ 435/6; 435/320.1; 536/23.1; 536/24.1
(58) Field of Search ................. 435/6, 320.1; 536/23.1, 536/24.1

(56) References Cited

U.S. PATENT DOCUMENTS 5,645,991 * 7/1997 Berg et al. .............................. 435/6
5,728,551 * 3/1998 Devine et al. ..................... 435/91.41

OTHER PUBLICATIONS

Morita et al. An in vitro system involving Tn3 transposase that catalyzes the formation of DNA deletions. Proc. Japan Acad. Vol. 65, Ser B, (1):1–4, Dec. 1989.*

Morita et al. Nested deletions from a fixed site as an aid to nucleotide sequencing: an in vitro system using Tn3 trasposase. DNA Research. vol. 3:431–433, Dec. 1996.*

LaBanca et al. Restriction map of a 35–kb HLA fragment constructed by nested deletion 'drop–out' mapping. Gene 164:335–339, Nov. 1, 1995.*

Sugino et al Jpn. J. Genet. (1983) 58, pp. 79–93 Deletion caused by Tn3: Correlation between deletion and transposition.

Sugino et al Gene. 148 (1994) 169–170 A new DNA cloning/sequencing vector with a built–in mechanism for generation of nested deletions using transposon Tn3*.

Wang et al Proc. Natl. Acad. Sci 90 7874–7878(Aug. 1993)pDual: A transposon–based cosmid cloning vector for generating nested deletions and DNA sequencing templates in vivo.

Ichikawa et al J. of Biological Chemistry 265, 31 pp. 18829–18832, 1990 In Vitro Transposition of Transposon Tn3*.

Morita et al J. Biochem 101 1253–1264 (1987) pp. 1253–1263 Overproduction and Purification of the Tn3 Transposase.

* cited by examiner

Primary Examiner—Robert A. Schwartzman
Assistant Examiner—William Sandals
(74) Attorney, Agent, or Firm—Nixon & Vanderhye P.C.

(57) ABSTRACT

The present invention provides a method for producing nested deletions in vitro in desired DNA, comprising:

1) preparing a vector containing a DNA fragment in which nested deletions are to be generated and the terminal repeat of a transposon;
2) incubating the vector in vitro with transposase and a DNA replication system;
3) obtaining the vector incorporating the DNA fragment with nested deletions as a reaction product; and optionally,
4) transforming a host cell with the reaction product and growing it; and
5) recovering a vector incorporating said DNA fragment with nested deletions from the grown host cell.

10 Claims, 2 Drawing Sheets

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: synthetic
      primer used for sequencing internal deletion
      products.

<400> SEQUENCE: 1
gaccaaaatc ccttaacg                                                  18

METHOD FOR PRODUCING DNA NESTED DELETIONS BY AN IN VITRO REACTION USING TRANSPOSASE

BACKGROUND OF THE INVENTION

The present invention relates to a method for generating DNA nested deletions by in vitro reactions.

The present invention also relates to a kit for use in said method for generating DNA nested deletions.

In genetic engineering technology, a desired DNA fragment is often manipulated by being insertedinto a vector. In such a case, it may be necessary to prepare the DNA insert in a length suitable for maniuplation.

For example, it is important to insert a DNA fragment of a suitable length into a vector, particularly in DNA sequencing techniques which can determine only a limited length of sequence at once. More specifically, the current DNA sequencing techniques can determine a sequence of at most about 1000 bases, usually only 300 to 400 bases at once. Therefore, longer fragments are sequenced by 1) subcloning, 2) primer walking, and 3) nested deletion or other methods. Among them, the nested deletion method is a technique which generates a number of nested deletions from a fixed site and it is more promising than the former two methods because a variety of deletion products can be conveniently obtained, as well as for other reasons. The nested deletion method hitherto known is performed in vitro by using exonuclease such as ExoIII or in vivo by using the terminal repeat of a transposon and transposase.

Transposons are a kind of movable genetic element and form a genetic unit which moves (transposes) from a portion of chromosomal DNA, plasmid DNA or viral DNA to another portion of the same or different DNA. They are widely distributed in bacteria, yeasts, maize, Drosophila, etc. The DNA site (target) to which they transpose is not fixed specifically, and it is presumed that they are able to transpose to any DNA site. Transposons are structurally characterized by an inverted repeat (IR) or a direct repeat at each end where recombination always occurs, indicating that this repeat has an important role in transposition. Transposons typically contain a gene responsible for the functions required for transposition or the expression of these functions.

Some transposons such as Tn3 and Tn1000 are known to function not only to bring about transposition of a gene but also to delete adjacent genes. Moreover, it was found that a mutation in the gene controlling transposition (tnpR) in a transposon increases the frequency of deletions as well as transposition reactions (Yoshinobu SUGINO and Hitoshi KAWASHIMA, Jpn. J. Genet. (1983) 58, pp. 79–93). A system for generating deletions in vivo has been developed (Sugino, Y. and Morita, M. 1994, Gene, 148, 169–170; and Wang, G. et al., Proc. Natl. Acad. Sci. USA (1993) 90, 7874–7878). This system is designed to insert a desired cloned DNA fragment into a vector having the terminal repeat of a transposon and transform said vector into *E. coli* which over expresses transposase to generate deletions from the terminal repeat of the transposon in *E. coli*. This system is commercially available as, for example, DELETION FACTORY® System from LIFE TECHNOLOGIES.

Although the conventional nested deletion methods are useful as described above, they involve problems due to in vivo reactions, e.g. they necessarily require a time for incubation and the desired gene may be denatured during reactions, etc. On the other hand, a transposon has been successfully transposed in vitro from a plasmid into λ DNA (Ichikawa, H. and Ohtubo, E. 1990, J. Biol. Chem., 265, 18829–18832). However, any method for generating nested deletions in vitro has not been known prior to the present invention, despite of a great need therefor.

SUMMARY OF THE INVENTION

An object of the present invention is to provide a method for producing nested deletions in vitro in a desired DNA, comprising:

1) preparing a vector containing a DNA fragment in which nested deletions are to be generated, and the terminal repeat of a transposon;
2) incubating said vector in vitro with transposase and a DNA replication system;
3) obtaining said vector incorporating said DNA fragment with nested deletions as a reaction product; and optionally,
4) transforming a host cell with said reaction product and growing it; and
5) recovering a vector incorporating said DNA fragment with nested deletions from the grown host cell.

Another object of the present invention is to provide kit for use in said method for generating DNA nested deletions, comprising transposase and a DNA replication system stored in a suitable container.

DETAILED DESCRIPTION OF THE INVENTION

Figure 1:
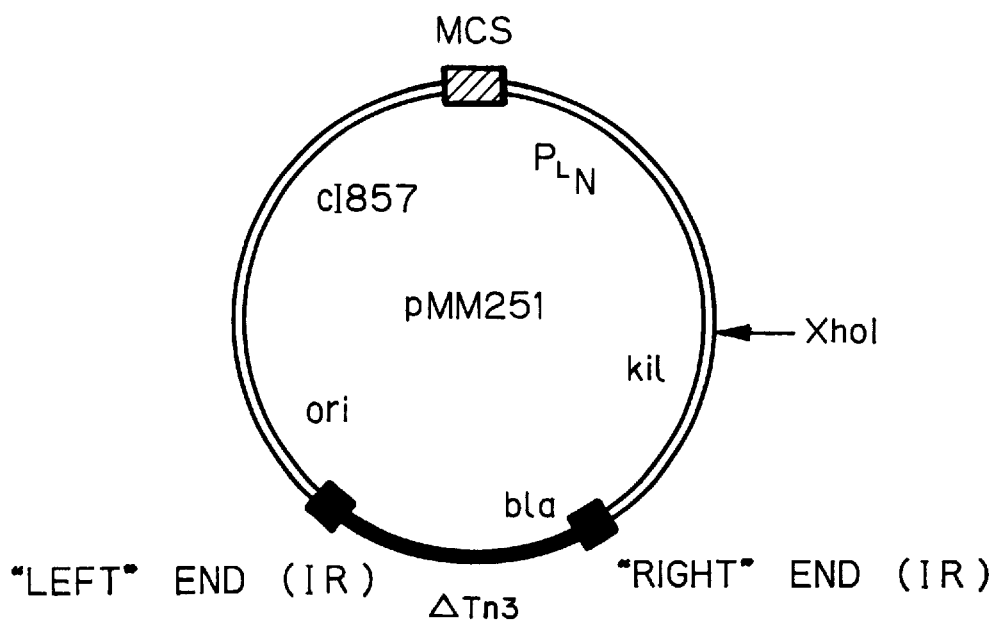
FIG. 1 shows a schematic representation of the structure of pMM251.

As a result of profound study to solve the above problems, we succeeded for the first time in producing DNA nested deletions by in vitro reactions using a fragment containing a DNA replication active element extracted from a host cell overexpressing transposase.

The method for producing DNA nested deletions according to the present invention comprises:

1) preparing a vector containing a DNA fragment in which nested deletions are to be generated, and the terminal repeat of a transposon;
2) incubating said vector in vitro with transposase and a DNA replication system;
3) obtaining said vector incorporating said DNA fragment with nested deletions as a reaction product; and optionally,
4) transforming a host cell with said reaction product and growing it; and
5) recovering a vector incorporating said DNA fragment with nested deletions from the grown host cell. Under the action of transposase, many DNA deletions occur starting from the terminal repeat and terminating at many different unfixed sites. A vector incorporating the DNA fragment with deletions can be detected by transforming the host cell with the reaction product. Essential elements of the present invention will now be explained in detail.

1) Vector

The vector used in the present invention contains a DNA fragment in which nested deletions are to be generated and the terminal repeat of a transposon. Said vector further contain an origin of replication for the replication in host cells. Preferred vectors are, for example, plasmid vectors, cosmid vectors, etc.

The terminal repeat of a transposon is preferably derived from, but not limited to, Tn3 and Tn1000 (also called as "γδ") (Sugino et al., 1994, Gene, 148, supra.; and Wang et al., 1993, supra.). These transposons lie on plasmids, phages or chromosomes of enterobacteria and greatly resemble each other. The terminal repeats of Tn3 and Tn1000 consist of 38 and 39 bp, respectively, and their base sequences also highly resemble each other. In addition to their transposition activity, these transposons are generally capable of forming a DNA deletion starting from the base adjacent to their own end and terminating at an unfixed external site on the DNA molecule in which they are located. The variant of Tn3 (ΔTn3) wherein the gene encoding transposase (tnpA) and the gene encoding its control factor (tnpR) have been modified to be deleted is more preferred, because such a variant itself generates no deletion (Yoshinobu SUGINO and Hitoshi KAWASHIMA, 1983, supra.). Other transposons than Tn3 and Tn1000 which can similarly generate a DNA deletion can also be applied in the present invention.

Insertion of the terminal repeat of a transposon into a vector can be performed by known techniques, for example, by linearizing the vector at an appropriate site by digestion with an appropriate restriction enzyme, and then ligating a DNA fragment containing the terminal repeat of the transposon with a DNA ligase or the like. Alternatively, a suitable vector containing the terminal repeat of a transposon may be used as disclosed in literatures of, for example, Sugino et al. (1994, supra.) and Wang et al. (1993, supra.).

The length of a fragment inserted into a vector is about 1000 to several tens of thousands of base pairs, and particularly, the present invention allows longer fragments of several tens of thousands of base pairs to be treated. The base sequence of the DNA fragment to be inserted is not specifically limited, but any desired DNA fragment can be inserted. The vector preferably has a multiple cloning site into which a desired DNA fragment can be inserted. Insertion of said DNA fragment into a vector can also be performed according to known techniques similarly to the insertion of a transposon.

According to the method of the present invention, a host cell is transformed with the reaction product after deletion reactions by in vitro incubation and grown to recover deletion products from grown transformants. Therefore, it is preferred that the vector further contains a marker gene for selectively detecting transformed host cells. Such a marker gene is well known to those skilled in the art, including a gene conferring resistance -to a drug such as ampicillin or non-auxotrophy on host cells. In those cases, only host cells transformed with the vector can be grown in a specific selective medium.

Preferably, the vector further contains a marker gene for selectively detecting only vectors partially or totally deleted resulting from a desired deletion from other vectors undeleted. The gene for detecting said deletion products includes a gene with which host cells are not viable under specific conditions. Such a gene is placed between the terminal repeat of a transposon and an end of the insert DNA fragment. Thus, a desired deletion occurs under said specific conditions so that only host cells transformed with a vector having a marker gene disabled can be selectively viable. Alternatively, a part of the immunity region of phage DNA may be inserted and subsequently cross-streaked against a suitable phage mutant to confirm the deletion of said region.

On the basis of the descriptions of the present specification, those skilled in the art may readily select a transposon, a marker gene, a gene for detecting deletion products and a vector carrying them which can be applied to the method for producing DNA deletions according to the present invention.

An example of a preferred vector for the present invention is, but not limited to, pMM251 described by Sugino et al. (1994) supra (FIG. 1). pMM251 contains ΔTn3, the bla gene serving as a marker gene for transformants, a combination of the kil and cI857 genes derived from λ phage DNA serving as marker genes for detecting deletion products, and the N gene. The bla gene confers ampicillin resistance on host cells. If DNA of pMM251 is not altered, even transformed host cells form no colony at higher temperatures (32 to 42° C., preferably about 42° C.) than ordinary incubation temperatures. This is because the kil gene is repressed by the cI gene under ordinary incubation conditions but derepressed from the cI gene and expressed to cause death of host bacteria under high temperature conditions. However, transformants will be formed even at high temperatures if a deletion occurs from the terminal repeat of ΔTn3 over the kil gene. The phage having an appropriate genotype (for example, λimm434Nam7am53) can be rescued in the presence of the N gene, but can not be rescured if the N gene is deleted. It is also possible to examine whether or not said cI gene has been deleted by using, for example, λcI60, etc.

The vector DNA is used at a conentration of about 0.04 $\mu g/\mu l$ or less during deletion reactions.

2) Transposase

Transposase is necessary to form a deletion. Purified or partially purified transposase may be used, or a culture or extract of the overexpression products of an expression vector incorporating a gene for coding transposase in a host cell may be used. Those skilled in the art can perform purification or overexpression of transposase by known methods.

For example, Tn3 transposase can be expressed in a large amount by introducing the plasmid pMM240 which overexpresses the tnpA gene encoding Tn3 transposase into, for example, the host E. coli DOO (Morita, M., Tsunasawa, S. and Sugino, Y., 1987, J. Biochem., 101, 1253–1264).

3) DNA replication system

Transposition reactions of transposase are inhibited by replacing deoxyribonucleic acid required for DNA synthesis with dideoxyribonucleic acid or adding a DNA gyrase inhibitor required for unwinding of supercoils of DNA, such as novobiocin or oxophosphoric acid. This indicates that transposition reactions of transposase require DNA synthesis (Ichikawa et al., 1990, supra.). Similarly, deletion reactions also appear to require DNA synthesis.

Therefore, it is necessary to contain not only transposase but also a DNA replication system in a deletion reaction solution according to the method of the present invention. DNA replication is a complex reaction process which requires high accuracy primarily for copying the base sequence and imposes physical separation of the two strands of the parent molecule. It is thought that about 20 or more proteins are needed for DNA replication.

As used herein, the "DNA replication system" means a group of at least minimum of proteins which are necessary for deletion reactions of transposase and which are responsible for DNA replication, such as DNA polymerase, topoisomerase, etc. At present, the system required for DNA replication activity has not been wholly explained, and cell extracts are commonly used. However, the DNA replication system of the present invention is not limited to cell extracts, but includes any system comprising a group of minimum of proteins required for DNA replication.

Those skilled in the art can use a fraction having DNA replication activity extracted from, for example, *E.coli* host cells according to known procedures (Ichikawa et al., 1990, supra.). A typical example thereof is the ammonium sulfate fraction described by Fullers et al. (Proc. Natl. Acad. Sci. U.S.A. 78, 7370–7374), i.e. fraction II.

A fraction containing a DNA replication system is advantageously obtained from host cells which have overexpressed transposase.

4) Deletion reactions

The reaction solution contains vector DNA, transposase, a DNA replication system, and optionally deoxyribonucleic acid (dNTP) required for DNA replication, a suitable energy donor (for example, creatine phosphate and creatine kinase, ATP, etc.), etc. The reaction is carried out at about 30 to 37° C., preferably about 30° C. for about 60 to 120 minutes, preferably about 120 minutes.

5) Detection of deletion products

Host cells are transformed with the deletion reaction products to detect desired deletion products. Transformation can be performed according to known methods by using a suitable host cell depending on the nature of the vector. A preferred host cell is *E. coli*. If the vector contains a marker gene for transformation, only transformed host cells can be selectively detected.

Detection of deletion products can be done by, for example, extracting vector DNA from host cells and determining its length by electrophoresis or the like. When the vector additionally contains a gene for detecting deletion products, host cells may be grown under specific conditions, for example, to select only vectors which lack said gene.

However, preferred deletion products containing a deletion of a desired insert DNA fragment can not readily be obtained with the reaction products as such because background noise is generally high due to secondary reactions. Thus, it is preferable to treat the reaction products with a restriction enzyme which cleaves only between the terminal repeat of a transposon and the insert before transformation takes place after deletion reactions. This step allows any vectors retaining a digestion site between the terminal repeat and the insert to be cleaved, and they are not transformed into host cells. This reduces the noise level due to mechanisms other than deletions from the terminal repeat of a transposon and remarkably facilitates detection and isolation of the desired deletion products. In case of Example 1 of the present specification, for example, the products were digested with the restriction enzyme XhoI which cleaves only between the cloned fragment and the ΔTn3 right end. As a result, background noise decreased from about $10^{-5}$ before treatment with the restriction enzyme to $10^{-6}$ or less after treatment.

Alternatively, when both ends of the intended insert DNA fragment have been treated with different restriction enzymes, these enzymes can be used for the same purpose. In Example 2 of the present specification, a KpnI-SmaI fragment was used as an insert and the deletion reaction products were digested with the restriction enzyme KpnI.

The method for producing DNA nested deletions by in vitro reactions using transposase according to the present invention is an excellent method with various advantages over the conventional methods for generating deletions.

At first, the procedure is simple as compared with the conventional in vitro reaction methods using exonuclease III, etc. Namely, the system using exonuclease III involves multiple reactions for different periods of time to obtain sufficiently different sizes of deletions as well as delicate enzymatic manipulations to create blunt ends. In contrast, the system of the present invention provides quite various sizes of deletions in a single run. Therefore, when the system is used for nucleic acid sequencing, for example, it is only necessary to randomly pick up a sufficient number of clones for obtaining enough various sizes to cover the entire length of the intended DNA fragment.

The present invention also has many advantages over the methods for producing deletions in vivo by a transposon. At first, only a short time is required enough to remarkably save time. When the in vitro reaction system is used, the time needed to generate and recover deletions is at least 2 days shorter as compared with in vivo systems because active preparations containing transposase can be frozen for several months. Secondly, the present invention can be applied to even genes which may alter DNA in living cells. Thirdly, the procedure to obtain deletion products is more convenient and background noise can be reduced. Fourthly, the amount of transposase acting on DNA or the like can be controlled to give more homogeneous deletion patterns.

The deletion products obtained by the present invention are widely useful in genetic engineering technology for DNA sequencing or other purposes where a DNA insert is to be prepared in an appropriate length.

The following examples illustrate the present invention, but are not intended to limit the technical scope thereof. Those skilled in the art can readily add modifications or changes to the present invention in the light of the description of the present specification, and they are also included in the technical scope of the present invention.

EXAMPLES

Example 1

1) Vector DNA

As a vector, the plasmid vector pMM251 containing ΔTn3 with the kil, N and cI857 genes of λ phage was used (Sugino et al., 1994, supra.). In pMM251, the $P_L$ promoter and the kil gene of λ phage lie between the right IR of ΔTn3 which is a variant of transposon Tn3 containing deletions in the tnpA and tnpR genes (Morita et al., 1987, supra.) and the MCS (multiple cloning site) derived from pUC18. Transcription from the $P_L$ promoter is repressed by the thermosensitive λ repressor encoded by the cI857 gene. The $P_L$-kil region and the cI857 gene constitute a mechanism for selecting deletions catalyzed by Tn3 transposase. At 42° C., only cells bearing the vector which has lost the kil gene function can survive.

A fragment of λ phage DNA digested with the restriction enzyme StuI (1519 bp) was inserted into the SmaI site of the MSC of said vector and this construct was used as vector DNA.

FIG. 1 shows a schematic representation of pMM251. In FIG. 1, the two inverted repeat sequences at both ends of ΔTn3 are indicated by black squares. The "bla" is an ampicillin-resistant gene and the "ori" is an origin of replication. The MCS derived from pUC18 is indicated by a stripped box. The XhoI site to be cleaved after reaction is indicated by an arrow.

2) Transposase active element and DNA replication active fraction

The plasmid pMM240 overexpressing Tn3 transposase (Morita et al., 1987, supra.) was intoduced into the host *E.coli* strain D110 polA$^+$ to prepare an ammonium sulfate fraction having DNA replication activity from this bacterium. The preparation was performed according to the procedure described by Ichikawa et al. (1990, supra.).

This preparation contained about 100 mg/ml of protein and 100 μg/ml of Tn3 transposase. The transposase content was determined by SDS polyacrylamide gel electrophoresis and silver staining according to the description of Morita et al. (1987, supra.).

3) Reaction conditions

The components shown below in Table 1 were reacted with each other at 30° C. for 120 minutes in a test tube (EPPENDORF TUBE™).

TABLE 1

| | |
|---|---|
| E. coli-derived extract containing a transposase active element and DNA replication activity | 5 µl |
| Vector DNA | 2 µg |
| Na-HEPES buffer (pH 7.6) | 25 mM |
| Magnesium acetate | 12 mM |
| DTT | 5 mM |
| KCl | 60 mM |
| ATP | 2 mM |
| dATP | 200 µM |
| dGTP | 200 µM |
| dCTP | 200 µM |
| dTTP | 200 µM |
| NAD | 40 µM |
| Bovine serum albumin (BSA) | 50 µg/ml |
| tRNA | 100 µg/ml |
| Polyvinyl alcohol | 2% |
| Creatine phosphate | 20 mM |
| Creatine kinase | 100 µg/ml |
| Total volume | 50 µl |

After reaction for 120 minutes, the reaction was stopped by adding 200 µl of 10 mM EDTA. To this mixture were added 25 µl of 0.55 M Tris-HCl (pH 8.8) and 2.2% sodium dodecyl sulfate (SDS), and the mixed solution was treated with phenol saturated with TE (10 mM Tris-HCl, pH 8.0, 1 mM EDTA). The DNA in the aqueous phase was ethanol precipitated to give purified DNA.

4) Restriction enzyme treatment to reduce backgrounds

No colony is formed at 42° C. with unmodified DNA even if transformation occurred. This is because the kil gene illustrated in 1) is derepressed from the cI gene so that it kills host cells. Transformants will be formed at 42° C. if a deletion occurs from the IR on the right of the figure over the kil gene. This is the principle of the method for detecting a vector containing a deletion.

However, preferred deletion products containing a deletion of a desired insert DNA fragment can not be readily obtained with the reaction products as such because background noises are more or less high due to secondary reactions. Thus, the reaction products are treated with a restriction enzyme which cleaves only between the IR and the insert after deletion reactions, in order to reduce background noise. In case of the vector of this example, the products were digested with the restriction enzyme XhoI which cleaved only between the cloned fragment and the Tn3 right end.

As will be described in 6), the background noises of temperature-resistant clones generated by mechanisms other than deletions from the Tn3 end were reduced to the level of about $10^{-6}$ or less of the total number of molecules by this restriction enzyme treatment.

5) Transformation

After the restriction enzyme treatment, the reaction products were purified and again ethanol precipitated and dissolved into 10 µl of water. 2 µl of each DNA solution (about 0.12 µg DNA) was mixed with the E. coli strain DOO cells in 80 µl of glycerol (Morita et al., 1987, supra.) and electroporated with GENE PULSER® (BIO-RAD). The procedure of electroporation is described by Dower et al. (Nucleic Acids Res. 16, 6127–6145, 1988). This mixture was mixed with 1 ml of SOC (2% BACTO TRYPTON™, 0.5% Bacto yeast extract, 10 mM NaCl, 2.5 mM KCl, 10 mM MgCl, 10 mM MgSO$_4$, 20 mM glucose), and shaken at 30° C. for 60 minutes. Then, 10 µl of the culture was plated on agar plates containing 100 µg/ml ampicillin at 30° C., while the rest of the culture was centrifuged and similarly plated on plates at 42° C. The incubation at 30° C. was intended to assess the transformation efficiency and the effect of the restriction enzyme treatment of the deletion products.

6) Electrophoresis of vector DNA and activity tests of the N and cI857 genes

A total of 72 colonies were obtained from the plates incubated at 42° C. for a total of 0.56 µg of DNA. At 30° C., $1.3 \times 10^4$ colonies were obtained per µg of DNA. This corresponds to a reduction by $4.2 \times 10^{-4}$ in the number of colonies obtained at 30° C. per µg of the sample DNA which has not been treated with XhoI.

Plasmid DNA was purified from each colony and the sizes of the plasmids were determined by electrophoresis. About 50 ng of plasmid DNA was electrophoresed on 0.7% agarose gels in TBE buffer (90 mM Tris-borate, 2 mM EDTA) at 50 V for 12 hours.

On the other hand, the activities of the vector-derived N and cI857 genes of λ phage were assesed. Specifically, transformants at 42° C. were checked for their cI857 and N gene status by cross streaking against λ cI60 at 30° C. and λ imm434Nam7am53 at 42° C., respectively. λ cI60-sensitive transformants are taken to have partially or wholly lost the cI857 gene. Similarly, transformants which are not sensitive to λ imm434Nam7am53 are also taken to have partially or wholly lost the N gene.

7) Results

The results of electrophoresis and the results of the cI and N gene activity tests were compared and examined.

Ten out of 72 plasmids were longer than 7.9 kb, but had lost the cI$^+$ activity. This means that these plasmids did not result from deletions from the IR at the right end of Tn3. One of them had also lost the N gene activity. Accordingly, these 10 clones were not examined furthermore.

Figure 2:
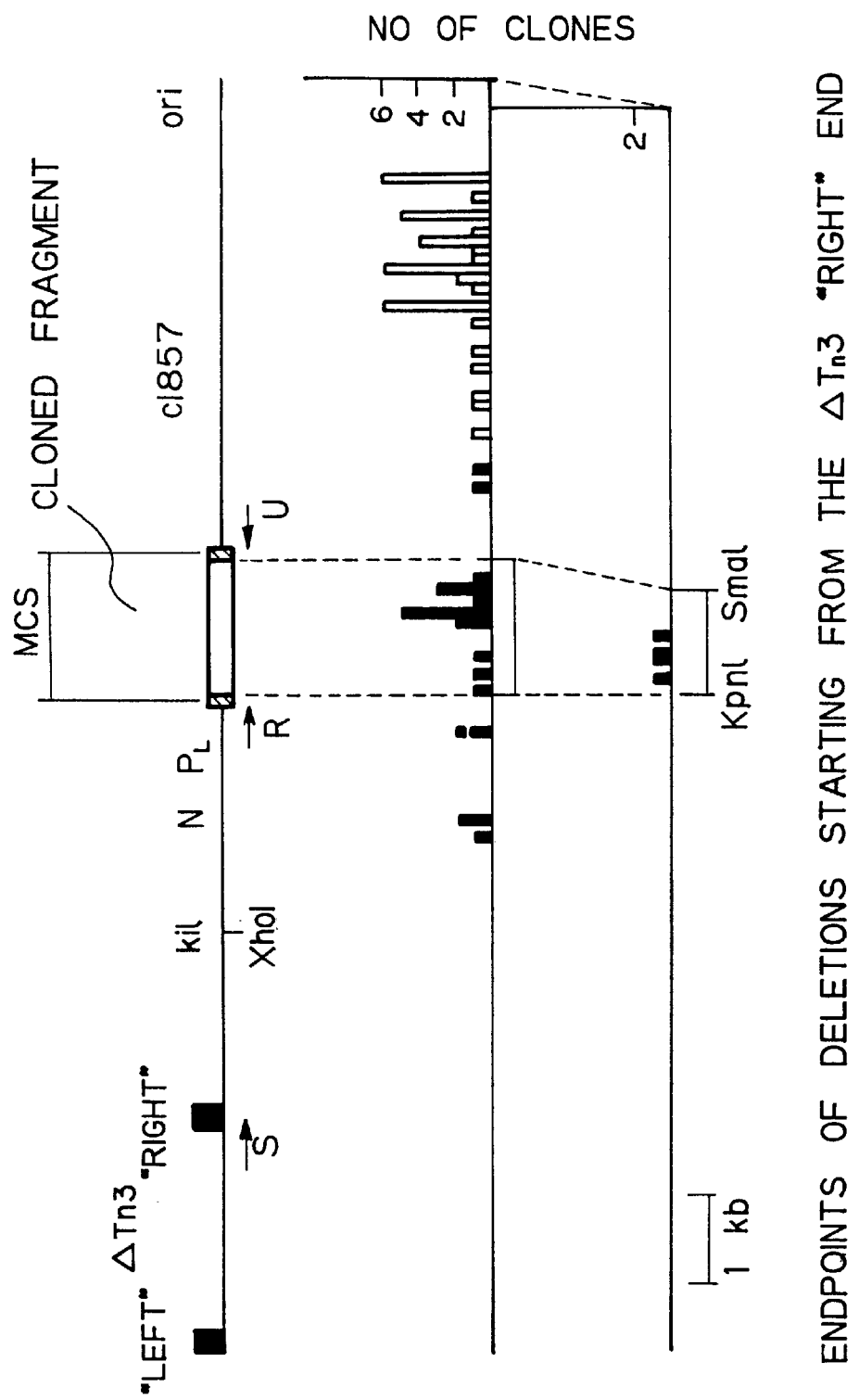
FIG. 2 shows distribution of endpoints of deletions starting from the right" end of ΔTn3.

Distribution of the endpoints of deletions from the "right" end of ΔTn3 of the remaining 62 plasmids is shown in FIG. 2 (middle).

FIG. 2 shows a linear map of pMM251 at the top. S represents the synthetic primer (5'-GACCAAAATCCCTTAACG) SEQ ID NO:1 for sequencing internal deletion products. U and R are the universal and reverse primers for sequencing from the two ends of the insert, respectively. Positions of deletion endpoints starting from the Tn3 "right" end and the number of clones obtained are shown in the middle. Black and white bars show that the clones are immune or sensitive to λ cI60, respectively.

A plasmid containing a deletion from the Tn3 end to a point within the insert should have a length of 7.937 kb to 9.456 kb and should lack the N gene but retain the I857 gene. FIG. 2 shows that 15 plasmids of 8.2 kb to 9.5 kb in size with deletion endpoints separated by 0.1 kb to 0.4 kb meet these requirements. They would be sufficient to provide templates for sequencing of the whole 1519-bp insert.

Other 5 plasmids are longer than 10 kb and retain the cI857 gene. They are deletion products in which deletion endpoints did not reach the insert. The other 42 plasmids are shorter than the prescribed size, which means that these clones lack the entire insert. Forty of them had lost the cI857 gene and were shorter than 6.6 kb, while 2 relatively large (7.0 kb and 7.2 kb) plasmids retain the cI857 gene, indicating that their endpoints lie between the 3' end of the insert and the cI857 gene (FIG. 2).

In this example, λ-sensitive clones, i.e. the plasmids which lack the entire insert and the cI857 gene are not useful for sequencing. However, these clones reveal that deletion endpoints are distributed more or less evenly and at random not only within but also on both sides of the insert, i.e. almost all over the 8.5 kb region between the XhoI site and the ori (origin of replicating as shown in FIG. 2 (middle). These data indicate that a larger insert would also give similar deletion products suitable for sequencing. This is also in accord with the in vivo data that Tn3 shows little target site specificity or regional specificity.

Example 2

Experiments were performed in the same way as described in Example 1 using a 1.2-kb KpnI-SmaI fragment from the crp⁻ gene of *E. coli* as an insert DNA fragment. In this example, the reaction products were digested with the restriction enzyme KpnI instead of XhoI and used for transformation. KpnI cleaves the reaction products at the "left" end of the insert DNA.

The results of electrophoresis and cI and N gene activity tests are shown at the bottom of FIG. 2. Five λ-immune clones were obtained for 0.28 μg of DNA from agar plates containing ampicillin at 42° C. One of them was shown not to contain any deletion from the Tn3 end from its size and KpnI digestion. Four plasmids of 8.9 kb, 8.7 kb, 8.6 kb and 8.4 kb, each containing a deletion starting from the "right" end of Tn3 and ending within the insert were obtained. Together with the original plasmid capable of sequencing the insert from both ends, three of the deleted clones suffice to determine the entire base sequence of this insert.

The results of Examples 1 and 2 show that the intended insert DNA fragment could be randomly deleted by the method for generating deletions in vitro of the present invention. Thus, we could obtain sufficient deletion products to effectively sequence large DNA which can not be sequenced in a single step. Moreover, the method of the present invention is also effective when the insert DNA fragment is longer as shown in the middle of FIG. 2.

2) incubating said vector in vitro with a transposase and a DNA replication system, in a reaction solution containing 0.002 μg/μl to 0.04 μg/μl of said vector, producing a product;

3) digesting the product of step 2) with a restriction enzyme which cleaves said vector containing the terminal repeats of the transposon and the contained DNA fragment only between one of the terminal repeats of the transposon and the contained DNA fragment;

4) obtaining said vector containing said DNA fragment with nested deletions as a reaction product; and optionally, 5) transforming a host cell with said reaction product and growing it; and 6) recovering said reaction product which is the vector containing said DNA fragment with nested deletions from the grown host cell.

2. The method of claim 1, wherein the terminal repeats of a transposon are that of Tn3 transposon or Tn1000 transposon.

3. The method of claim 1 wherein the transposase has been prepared from a host cell bearing an expression vector producing transposase.

4. The method of claim 1 wherein the transposase is purified transposease.

5. The method of claim 1, wherein the incubation of step 2) is carried out at 30 to 37° C. for 60 to 120 minutes.

6. The method of claim 1 wherein the reaction solution of step 2) further contains deoxyribonucleotides required for DNA synthesis and an energy donor.

7. A kit for use in the method of claim 1 comprising a transposase and a DNA replication system stored in a suitable container, and a vector containing the terminal repeats of a transposon, a buffer and optionally deoxyribonucleotides required for DNA synthesis each in a separate container or all in the same container.

8. The method of claim 1, wherein the vector further contains a marker gene for detecting a deletion.

9. The method of claim 8, wherein the marker gene is a combination of the kil gene and the cI857 gene of λ phage.

What is claimed is:

1. A method for producing nested deletions in vitro in a desired DNA, comprising:

1) preparing a vector containing a DNA fragment in which nested deletions are to he generated, and terminal repeats of a transposon;

10. A method for producing nested deletions in vitro in a desired DNA, comprising:

1) preparing a vector containing a DNA fragment in which nested deletions are to be generated, and terminal repeats of a transposon;

2) incubating said vector in vitro with transposase and a DNA replication system in a reaction solution containing 0.002 µg/µl to 0.04 µg/µl of said vector, producing a product;

3) digesting the product of step 2) with a restriction enzyme which cleaves said vector containing the terminal repeats of the transposon and the contained DNA fragment only between one of the terminal repeats of the transposon and the contained DNA fragment;

4) obtaining said vector containing said DNA fragment with nested deletions as a reaction product;

5) transforming a host cell with said reaction product and growing it; and 6) recovering said reaction product which is the vector containing said DNA fragment with nested deletions from the grown host cell.

* * * * *